United States Patent [19]

Brown

[11] 4,349,553
[45] Sep. 14, 1982

[54] SPIRO-CYCLOPROPYL AMIDINOHYDRAZONES, AND USE AS INSECT AND FIRE ANT CONTROL AGENTS

[75] Inventor: Dale G. Brown, Hopewell, N.J.

[73] Assignee: American Cyanamid Company, Stamford, Conn.

[21] Appl. No.: 149,403

[22] Filed: May 13, 1980

[51] Int. Cl.$^3$ .................... A01N 43/54; C07D 239/18
[52] U.S. Cl. .................................... 424/251; 544/231; 542/401
[58] Field of Search ...................... 544/330, 332, 231; 424/251; 542/401

[56] References Cited

U.S. PATENT DOCUMENTS 3,723,454  3/1973  Ost et al. ............................. 544/231
3,878,201  4/1975  Tomcfcik ............................. 424/251
4,087,525  5/1978  Lovell ............................. 424/273 R Primary Examiner—David B. Springer
Attorney, Agent, or Firm—Thomas J. Monahan; H. G. Jackson

[57] ABSTRACT

There are provided certain spiro-cyclopropyl amidinohydrazones, and methods of use of the compounds for the control of insects, especially Lepidopterous insects, and for the control of ants, Family Formicidae, especially fire ants.

23 Claims, No Drawings

SPIRO-CYCLOPROPYL AMIDINOHYDRAZONES, AND USE AS INSECT AND FIRE ANT CONTROL AGENTS

The present invention relates to insecticidal compounds of formula (1)

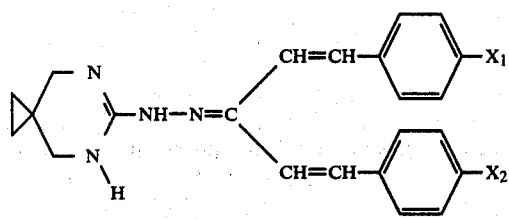

wherein $X_1$ and $X_2$ each are halogen, $CHF_2O$, $CF_3O$, $CHF_2CF_2O$, $CHF_2S$, $C_1-C_3$ alkoxy or $C_2-C_3$ alkyl.

Art of interest is in U.S. Pat. Nos. 3,878,201 and 4,087,525.

A preferred group of compounds represented by formula (1) are those wherein $X_1$ and $X_2$ each are selected from Br, Cl, $CF_3$, $CHF_2O$ and $CF_3O$.

A more preferred group of compounds represented by formula (1) are those wherein both $X_1$ and $X_2$ are the same, and are selected from Br, Cl, $CF_3$, $CHF_2O$ and $CF_3O$.

The above compounds (1) may be prepared by the route graphically illustrated and discussed as follows:

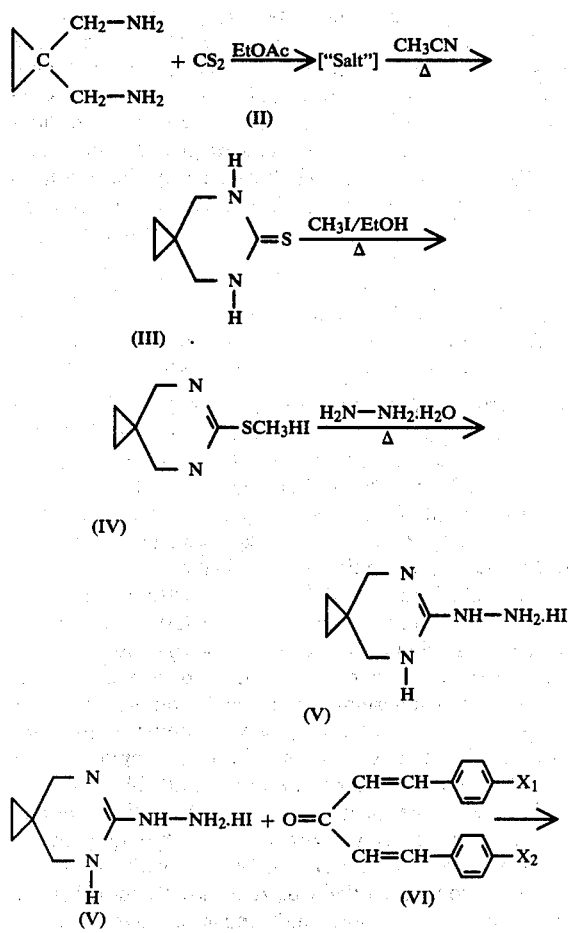

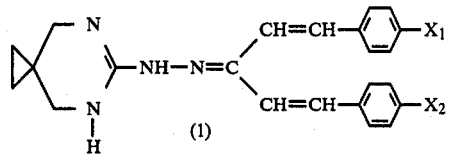

wherein in the above reaction sequence, $X_1$ and $X_2$ are as hereinabove defined.

Thus, the appropriate diamine (1) is reacted with an equimolar, or preferably excess amount of carbon disulfide in the presence of an inert solvent such as ethyl acetate in the temperature range of from about 10° C. to about 30° C. for a period of time sufficient to essentially complete the reaction. The isolated reaction product ("Salt") is then reslurried in an inert solvent such as acetonitrile and the slurry heated at reflux for a period of time sufficient to essentially complete the reaction and recover the "thione" (III). Heating this "thione" (III) with methyl iodide in the presence of a solvent such as ethanol yields the hydriodide salt of the corresponding methylthio compound (IV). Next, this compound (IV) is reacted with an equimolar or excess amount of hydrazine hydrate in the presence of an alcohol such as isopropyl alcohol at reflux to afford the hydrazine (V). Condensation of this hydrazine (V) with an equimolar amount of the appropriate ketone in absolute alcohol or another inert solvent affords the desired product of formula (I).

By the above reaction scheme, 1,1-cyclopropanedimethanamine is reacted with carbon disulfide to yield 5,7-diazaspiro[2.5]octane-6-thione. Alkylation of this thione with methyl iodide affords 6-(methylthio)-5,7-diazaspiro[2.5]-oct-5-ene, hydriodide. Reaction of this compound with hydrazine hydrate yields 6-hydrazino-5,7-diazaspiro[2.5]oct-5-ene hydriodide. Finally, condensation of this hydrazine with 1,5-bis(α,α,α-trifluoro-p-tolyl)-1,4-pentadien-3-one yields the desired formula (1) compound: 1,5-bis(α,α,α-trifluoro-p-tolyl)-1,4-pentadien-3-one 5,7-diazaspiro[2.5]-oct-5-en-6-ylhydrazone.

Advantageously the compounds of this invention find utility in controlling insects, particularly lepidopterous insects, and ants, Family Formicidae, by contacting the insects, and/or applying to their habitat or food supply, an insecticidally effective amount of a compound of formula (1)

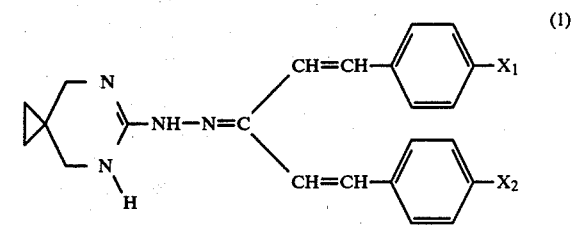

wherein, $X_1$ and $X_2$ are as hereinabove defined.

Further, the invention finds utility in protecting agronomic crops, trees, shrubs, ornamentals, and the like from attack by insects, by applying to the crops an insecticidally effective amount of a compound having the above-identified structure. In practice, from about 0.14 kg/hectare to 11.2 kg/hectare, and preferably 0.56 kg/hectare to 4.48 kg/hectare of a formula (1) hydrazone is effective for insect control and/or for crop protection.

The desired pentadienone hydrazones (1) can be applied in either liquid or solid form. For instance, they may be applied in solid form as dusts or dust concentrates, or in liquid form as emulsifiable concentrates, flowable formulations or wettable powders which are dispersed in water or some other inexpensive liquid for application as a finely divided spray.

The formula (1) compounds may also be prepared in the form of an attractant bait which is distributed in the locus or habitat of the insects sought to be controlled.

A typical emulsifiable concentrate can be prepared by admixing from about 12% to 29% by weight of pentadienone hydrazone, about 8% to 12% by weight of a blend on nonionic emulsifiers such as TMulz 339 (sold by Thompson-Hayward of Kansas City, Kans.), or polyoxyethylene derivatives and blends with alkyl aryl sulfonates, and about 59% to 80% by weight of cyclohexanone or a heavy aromatic solvent having a mixed aniline point between −1° C. and 35.0° C., a specific gravity between 0.880 and 1.5 at 15.5°/15.5° C. and an aromatic content of 60% to 100%. The formulations provide from 119.8 g/liter to 239.6 g/liter of active compound and are generally diluted with water for application as a dilute liquid. However, said formulations can also be applied in the form of undiluted discrete droplets as low volume or ultra-low volume sprays. For such application, the emulsifiable concentrate is usually applied with apparatus designed to disperse the liquid in the form of finely divided discrete droplets having a mass median diameter of from 25 to 150 microns.

A typical wettable powder formulation can be prepared by grinding together about 34% by weight of a synthetic calcium silicate, 12% by weight of a dispersing agent such as sodium lignosulfonate, 4% by weight of a wetting agent such as an alkyl aryl sulfonate, and 50% by weight of pentadienone hydrazone. Such formulation is generally dispersed in water for application as a liquid spray.

The compounds of this invention are active against Lepidopterous larvae such as southern armyworms [*Spodoptera eridania* (Cramer)], cabbage loopers [*Trichoplusia ni* (Hubner)] tobacco budworms [*Heliothis virescens* (Fabricius)], and the like, at 10 to 1000 ppm rates. They do not appear to be especially toxic to most beneficial insects and thus are useful for pest management and integrated control programs. Moreover, these compounds show virtually no phytotoxicity to plants at rates of application up to 11.2 kg/hectare.

Advantageously, the formula (1) pentadienone hydrazone compounds of the present invention are active as stomach poisons. Thus, they are effective against insects with chewing mouth parts (Orthopterous insects such as cockroaches, grasshoppers, crickets and Isopterous insects such as termites). They are effective for the control of fire ants, such as the southern fire ant, *Solenopsis xyloni*, the black imported fire ant, *Solenopsis richteri*, and the red imported fire ant, *Solenopsis invicta*. They are also effective for the control of ants such as the big-headed ant, *Pheidole megaphala*, and the Argentine ant, *Iridomyrmax humilis*, that are dominant pests in pineapple and sugarcane fields, and for the control of many species of ants that are classified under the general category of household ant. Ants are serious economic and public health pests. Serious problems created by fire ants include stinging of humans and livestock, feeding on plants, particularly on seedlings and on germinating seeds, damage to farm machinery that strike ant mounds, loss of crops and refusal of workers to enter infested fields to cultivate and harvest crops. Ants invade houses, crawl over food, carry bits of food to their nests and also cause damage by establishing their nests in the woodwork of houses and other wooden buildings.

Control of these pests can be achieved with treated baits that are distributed in or adjacent to the infested area, such as pasture, park dwellings or other locations in which ant control is desired, and made available to worker ants. The workers carry the treated bait to the colony where it is consumed by the queens and the young ants, leading to their destruction.

In practice, generally from about 1.25 g/ha to 75.0 g/ha, and preferably from 2.5 g/ha to 37.5 g/ha, of the pentadienone hydrazone is effective for fire ant control and/or for crop protection from ants and about 0.0625% to 4% by weight, and preferably 0.125% to 2.0% by weight of the pentadienone hydrazone is effective for the control of house ants and/or insects that are controlled by bait.

Baits can be prepared, for example, by admixing said formula (I) compounds with peanut butter or citrus pulp, vegetable oils such as soybean oil, animal fats such as lard and tallow, and with or without an organic filler such as bran, and/or an attractant such as lecithin. The composition is then placed in soda straws or on a carrier such as puffed grain, corncob grits and/or starch matrix and distributed in the area of the colony or infestation. Use of these baits has particular advantage, since such method of distribution poses little or no hazard to non-target organisms that may frequent the infested area.

The invention is further illustrated by the examples set forth below which are provided only by way of illustration and are not deemed to be limiting thereof.

EXAMPLE 1

Preparation of
1,5-bis($\alpha,\alpha,\alpha$-trifluoro-p-tolyl)-1,4-pentadien-3-one-5,7-diazaspiro[2.5]oct-5-en-6-ylhydrazone A mixture of 1,5-bis($\alpha,\alpha,\alpha$-trifluoro-p-tolyl)-1,4-pentadien-3-one (3.7 g; 0.01 mol), 6-hydrazino-5,7-diazaspiro[2.5[oct-5-ene hydriodide (2.68 g; 0.0099 mol) and absolute ethanol (125 ml) is stirred with 3 drops of concentrated HI and heated at reflux for 5 hours. The reaction mixture is then cooled down and the precipitated light-yellow solid collected by filtration.

The solid is mixed with saturated sodium carbonate solution (100 ml) and ethyl acetate (200 ml) and the mixture stirred until the upper (organic) phase becomes homogeneous. The organic phase is then separated, dried over magnesium sulfate, and evaporated under vacuum to give 3.5 g of glassy yellow-orange solid. Recrystallization of this solid from isopropyl alcohol affords a fine, yellow powder, m.p. 140°–141.5° C.

By the above procedure, but substituting various ketones for 1,5-bis($\alpha,\alpha,\alpha$-trifluoro-p-tolyl)-1,4-pentadien-3-one, the corresponding 5,7-diazaspiro[2.5]oct-5-en-6-ylhydrazones are obtained. These are listed in Table I together with the compound prepared above (No. 1).

TABLE I

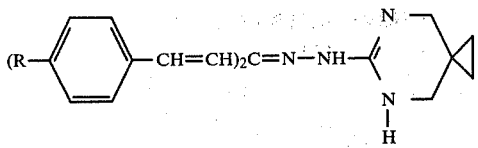

(R—⟨phenyl⟩—CH=CH)₂C=N—NH—⟨spiro structure with N, N-H⟩

| No | R | m.p. °C. | N.M.R./CDCl₃ in δ vs. TMS —N—CH₂ | ⟨spiro⟩ | Calculated C | H | N | Found C | H | N |
|---|---|---|---|---|---|---|---|---|---|---|
| 1 | CF₃ | 140–141.5 | 3.10 | 0.53 | 60.97 | 4.50 | 11.38 | 58.23 | 4.76 | 10.70 |
| 2 | Cl | 191.5–193 | 3.01 | 0.51 | 64.94 | 5.21 | 13.17 | 65.13 | 5.41 | 12.79 |
| 3 | CF₃O | 174–176 | 3.03 | 0.47 | 57.25 | 4.23 | 10.68 | 56.71 | 4.35 | 10.56 |
| 4 | CF₂HO | 158–159.5 | 3.00 | 0.41 | 61.47 | 4.95 | 11.47 | 61.03 | 4.80 | 11.41 |
| 5 | Br | 199–201 | 3.07 | 0.50 | 53.71 | 4.31 | 10.89 | 53.56 | 4.36 | 10.69 |

Similarly, by the above procedure, but substituting 1,5-bis(p-methoxyphenyl)-1,4-pentadien-3-one, 1,5-bis(p-ethylphenyl)-1,4-pentadien-3-one, 1,5-bis[p-(1,1,2,2-tetrafluoroethoxy)phenyl]-1,4-pentadien-3-one and 1,5-bis-p-(difluoromethylthio)phenyl-1,4-pentadien-3-one for 1,5-bis(α,α,α-trifluoro-p-tolyl)-1,4-pentadien-3-one, the corresponding hydrazones: 1,5-bis(p-methoxyphenyl)-1,4-pentadien-3-one-5,7-diazaspiro[2.5]oct-5-en-6-ylhydrazone, 1,5-bis(p-ethylphenyl)-1,4-pentadien-3-one-5,7-diazaspiro[2.5]oct-5-en-6-ylhydrazone; 1,5-bis[p-(1,1,2,2-tetrafluoroethoxy)phenyl]-1,4-pentadien-3-one-5,7-diazaspiro[2.5]oct-5-en-6-ylhydrazone and 1,5-bis[p-(difluoromethylthio)phenyl]-1,4-pentadien-3-one-5,7-diazaspiro[2.5]oct-5-en-6-ylhydrazone can be prepared, respectively.

EXAMPLE 2

Preparation of 6-Hydrazino-5,7-diazaspiro[2.5]oct-5-ene-hydriodide

The hydrogen iodide salt of 6-(methylthio)-5,7-diazaspiro[2.5]oct-5-ene (3.58 g; 0.0478 mol) is added to a solution of hydrazine hydrate (2.78 g; 0.556 mol) in isopropyl alcohol (40 ml) and the mixture heated at reflux for 4.5 hours. The heating is then stopped and heptane added to the reaction mixture to the cloud point. The mixture is then cooled and crystallization initiated by scratching the inner walls of the reaction vessel. The precipitated crystalline solids are filtered and dried under vacuum at 65° C. to afford 12.33 g (96.5% yield) of title product, m.p. 146°–147.5° C. NMR DMSO-D6. Cyclopropyl singlet (4H) 0.56 δ vs. TMS.

By the above procedure, but substituting 7-(methylthio)-6,8-diazaspiro[3.5]non-6-ene, and 8-(methylthio)-7,9-diazaspiro[4.5]dec-8-ene for 6-(methylthio)-5,7-diazaspiro[2.5]oct-5-ene, the respective hydrazines: 7-hydrazino-6,8-diazaspiro[3.5]non-6-ene and 8-hydrazino-7,9-diazaspiro[4.5]dec-8-ene can be prepared.

EXAMPLE 3

Preparation of 6-(Methylthio)-5,7-diazaspiro[2.5]oct-5-ene-hydriodide

A mixture of 5,7-diazaspiro[2.5]octane-6-thione (7.53 g; 0.053 mol), methyl iodide (8.43 g; 0.0594 mol) and absolute ethanol (26 ml) is stirred and heated at 45° C. for one hour until the reaction mixture becomes straw colored and homogeneous. Ethyl acetate is added with cooling, the precipitated crystalline material is collected and dried to afford 14.05 g (93.5% yield) of title product, m.p. 128°–130° C.

By the above procedure, but substituting 6,8-diazaspiro[3.5]nonane-7-thione and 7,9-diazaspiro[4.5]decane-8-thione for 5,7-diazaspiro[2.5]octane-6-thione, the corresponding methylthio compounds: 7-(methylthio)-6,8-diazaspiro[3.5]non-6-ene and 8-(methylthio)-7,9-diazaspiro[4.5]dec-7-ene can be prepared.

EXAMPLE 4

Preparation of 5,7-Diazaspiro[2.5]octane-6-thione

A solution of carbon disulfide (8.2 g; 0.108 mol) in ethyl acetate (10 ml) is added to a stirred solution of 1,1-cyclopropanedimethanamine while maintaining the reaction temperature at 12°–15° C. After 30 minutes, the mixture is allowed to warm up to room temperature for 24 hours. The precipitated white solid is filtered to yield 15.6 g of salt, m.p. 135° C. This salt is then suspended in acetonitrile (125 ml) and the suspension heated at reflux for 3 days. The solution is cooled, filtered and the isolated solid air dried to afford 8.22 g (65% yield) of title product, m.p. 264°–266° C. I.R. (Nujol mull) 1565 cm⁻¹.

By the above procedure, but substituting 1,1-cyclobutanedimethanamine and 1,1-cyclopentanedimethaneamine, the corresponding thiones: 6,8-diazaspiro[3.5]-nonane-7-thione, m.p. 220°–221.5° C.; and 7,9-diazaspiro-[4.5]decane-8-thione, m.p. 170°–172° C., are prepared.

EXAMPLE 5

Preparation of 1,5-bis(α,α,α-trifluoro-p-tolyl-1,4-pentadien-3-one-7,9-diazaspiro[4.5[dec-8-en-8-ylhydrazone A mixture of 1,5-bis(α,α,α-trifluoro-p-tolyl)-1,4-pentadien-3-one (3.7 g; 0.01 mol), 8-hydrazino-7,9-diazaspiro[4.5]dec-8-ene hydriodide (2.96 g; 0.01 mol), absolute ethanol (125 ml) and 3 drops of concentrated hydriodic acid is stirred and heated at reflux for 5.5 hours. Upon cooling a light yellow solid precipitates from the reaction mixture.

The solid is slurried with saturated sodium carbonate solution (100 ml) and ethyl acetate (200 ml) and the mixture stirred until the upper (organic) phase is homogeneous. The organic phase is then separated, dried over anhydrous magnesium sulfate and evaporated under vacuum to yield a glassy solid. Recrystallization of this solid from isopropyl alcohol affords the title product, m.p. 111°-113° C.

By the above procedure, but substituting 1,5-bis(p-chlorophenyl)-1,4-pentadien-3-one, the corresponding 7,9-diazaspiro[4.5]dec-8-en-8-ylhydrazone, m.p. 111°-118° C., is obtained.

EXAMPLE 6

Preparation of 1,5-bis(α,α,α-trifluoro-p-tolyl)-1,4-pentadien-3-one-6,8-diazaspiro 3.5 non-6-en-7-ylhydrazone A mixture of 1,5-bis(α,α,α-trifluoro-p-tolyl)-1,4-pentadien-3-one(5.66 g; 0.0153 mol), 7-hydrazino-6,8-diazaspiro[3.5]non-6-ene hydriodide (6.06 g; 0.0169 mol), isopropanol (50 ml) and 4 drops of concentrated hydriodic acid is stirred and heated at reflux for 20 hours. The solvent is then evaporated under vacuum to yield a yellow solid This solid is treated with a mixture of saturated sodium carbonate solution and ethyl acetate. Next, the upper (organic) phase is separated, dried over anhydrous magnesium sulfate and evaporated under vacuum to give a yellow solid. This solid is recrystallized from isopropyl alcohol to afford the title product, m.p. 204°-204.5° C.

EXAMPLE 7

Evaluation of the insecticidal activity of the compounds of the invention Methods 1. Tobacco budworm (*Heliothis virescens*), 1st instar.

Formulations

The compounds to be tested are dissolved in 50:50 acetone:water to yield solutions of 300,100 and 10 ppm concentration, respectively.

Insect preparation

Cheesecloth on which moth have oviposited is daily cut into 10-20 mm squares containing 50-100 eggs each. These squares are held at 21° C. for two days and at 24° C. for another day in order to coordinate hatch with testing times. Thus, the worms are 0-2 hours old at the time of use.

Test procedure

Cotton plants, with the first true leaf expanded about 6-7 cm in length are dipped in the test solutions, agitated for 3 seconds, and placed in a hood to dry. When dry, a leaf is removed from the plant and placed in an "8-ounce Dixie cup, #2168ST" (240 ml, 6 cm high, top diameter 9.5 cm, bottom diameter 8 cm) to which a 5 cm length of damp cotton dental wick has been previously added. A square of cheesecloth with newly hatched budworm larvae on it is placed on the treated leaf, a clear plastic lid (Dixie #3068G) is put on the cup, and the cups are held at 27° C. for two days. After two days mortality counts are made. The amount of feeding is also recorded. Where there is only trace to light feeding, the cup is held an extra day and the results recorded at that time.

2. Southern armyworm (*Spodoptera eridania*), 3rd instar.

Formulations

The compounds to be tested are dissolved in 2:1 acetone:water to yield solutions of 1000,100 and 10 ppm concentrations, respectively.

Plant preparation

Sieva lima bean plants are selected with primary leaves 7-8 cm long and cut back to one plant per plot.

Insect preparation

The bottom of a 100×10 mm petri dish is lined with a damp filter paper and ten 3rd instar larvae, each about 10 mm long, are added.

Test procedure

The bean plant is dipped in the test solution, agitated for 3 seconds and placed in a hood to dry. When dry, one leaf is removed from the plant and placed in the petri dish with the caterpillars. The dish is held at 27° C. The plant with the remaining leaf is held in the greenhouse under high intensity lights. Mortality counts are made after two days. If any reduction in feeding is noted, the dish is held for an additional day and reobserved. Mortality counts and reduced feeding are again determined, and the bean plants treated with compounds considered active are retained in the greenhouse exposed to high intensity lights for a 7-day residual activity test. One week after the original treatment, a leaf is removed from the plant and assayed again by the above procedure. The results yield a measure of the residual activity of the compound under test.

3. Mexican bean beetle (*Epilachna varivestis*), larva.

Formulations

The compounds to be tested are dissoved in 50:50 acetone:water to yield solutions of 300,100 and 10 ppm concentration, respectively.

Plant preparation

Sieva lima bean plants are selected with primary leaves 7-8 cm long, and cut back to one plant per pot.

Insect preparation

The bottom of a 100×10 mm petri dish is lined with a damp filter paper and ten last instar larvae, about 13 days old, are put in the dish.

Test procedure

The bean plant is dipped in the test solution, agitated for 3 seconds and placed in a hood to dry. When dry, one leaf is removed and placed in the petri dish with the insects. The 2nd leaf is added the next day. The dish and the remaining plant are held at 27° C. Mortality counts are made two days after treatment.

The test is retained until the adult beetles emerge, and is then reevaluated. At this time (about 9-10 days posttreatment) the dish is examined for dead larvae, dead pupae or adults, deformed pupae or adults, larval-pupal intermediates or pupal-adult intermediates, or any other interference with normal molting, transformation and emergence of pupae or adults.

4. Cotton boll weevil (*Anthonomus grandis*), adult.

Formulation

The compounds to be tested are dissolved in 2:1 acetone:water to yield solutions of 1000 and 100 ppm concentration.

Insect preparation

The bottom of a 100×10 mm petri dish is lined with a damp filter paper and ten adult boll weevils are added to the dish.

Test procedure

A cotton cotyledon is dipped in the test solution, agitated for 3 seconds and placed in a hood to dry. When dry, it is put in the petri dish with the insects. The dishes are held at 27° C. for two days.

Mortality counts are made, prodding each insect with a dull pencil point to distinguish dead ones from those "playing dead."

5. Tobacco budworm (*Heliothis virescens*), 3rd instar.

Formulation

The compounds to be tested are dissolved in 2:1 acetone:water to yield solutions of 1000,100 and 10 ppm concentration, respectively.

Test procedure

Cotton cotyledons are dipped in the solutions and dried in a hood. When dry, each cotyledon is cut into quarters, and ten sections are placed individually in 30 ml plastic medicine cups containing a 5–7 mm long piece of damp cotton dental wick. One 3rd instar budworm larva is added to each cup and a cardboard lid placed on the cup. The cups are held at 27° C. for 3 days. Mortality counts are then made.

6. Cabbage looper (*Trichoplusia ni*), 3rd instar.

Formulations

The compounds to be tested are dissolved in 2:1 acetone:water to yield solutions of 1000,100 and 10 ppm concentration, respectively.

Insect preparation

The bottom of a 100×10 mm petri dish is lined with a damp filter paper and ten 3rd instar larvae are added.

Test procedure

Cotton plants, with the first true leaf expanded about 7–8 cm in length are dipped in the test solutions, agitated for 3 seconds, and placed in a hood to dry. When dry, the leaf is placed in the petri dish with the insects. The dish is held at 27° C. for one or two days, and mortality counts are then made.

7. German cockroach (*Blattella germanica*), bait test.

Formulations

Cornmeal baits of 1000 ppm and 100 ppm are prepared by pipetting 1 ml of the appropriate concentration of a solution of test compounds onto 1 g of cornmeal in a 30 ml wide-mouth bottle. A gentle stream of air is passed into the bottle until the baits are dry.

Test procedure

To 1-pint wide-mouthed Mason jars (about 500 ml), each containing 1 g of bait prepared as above, are added ten adult male cockroaches (per jar) and a screen lid placed on the jars. After one day a small wad of cotton soaked in 10% honey solution is placed on the top of each screen lid. During the test the jars are held at 27° C.

One day posttreatment initial knockdown or kill is determined. Final observations are made four days posttreatment.

8. German cockroach (*Blattella germanica*), residue test.

Formulations

The compounds to be tested are dissolved in acetone to yield solutions of 1000 and 100 ppm concentration.

Test procedure

Petri dishes of 150×15 mm dimensions are used. One ml of the test solution is pipetted slowly over the bottom of the dish so as to give as uniform coverage as possible. By this method a deposit of about 1 mg/150 cm$^2$ is obtained when using a 1000 ppm test solution. The dishes are allowed to dry, following which ten adult male cockroaches are placed in each dish, the cover put on the petri dishes, and the dishes are then held at 27° C.

Treatments are observed at one day posttreatment for initial knockdown or kill. Final observations are made four days posttreatment.

The data obtained by the above tests are summarized in Table II, wherein it can be seen that the compounds of the invention effectively control insects, especially lepidopterous insects.

TABLE II

Evaluation of the insecticidal activity of the compounds of the invention represented by the formula:

$$(R-\phantom{x})\!\!-\!\!\bigcirc\!\!-\!\!CH=CH)_2C=N-NH-\!\!\!\underset{\underset{H}{N}}{\overset{N}{\diagdown}}\!\!\bigtriangleup$$

Percent[1] mortality counts are given at the parts per million (ppm) concentrations shown

| R | Tobacco budworm 1st instar -ppm- | | | Southern armyworm 3rd instar -ppm- | | | 7* days | Mexican bean beetle larva -ppm- | | | Boll weevil adult -ppm- | |
|---|---|---|---|---|---|---|---|---|---|---|---|---|
|   | 300 | 100 | 10 | 1000 | 100 | 10 |   | 300 | 100 | 10 | 1000 | 100 |
| CF$_3$ | 100 | 100 | 0 | 100 | 100 | 100 100 | 0 0 | 0 |   |   | 0 |   |
| CF$_3$O | 100 | 100 | 0 | 100 | 100 | 100 100 | 0 0 | 30 |   | 0 | 50 | 0 |
| Br | 100 | 100 | 65–75 | 100 | 100 | 100 100 | 0 0 0 | 0 |   |   | 100 |   |
| CHF$_2$ O | 0 |   |   | 100 | 80 | 0 | 0 | 0 |   |   | 0 |   |

TABLE II-continued

Evaluation of the insecticidal activity of the compounds of the invention represented by the formula:

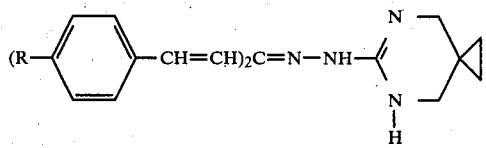

Percent[(1)] mortality counts are given at the parts per million (ppm) concentrations shown

| Cl | 100 | 85-95 | 0 | 100 | 100 | 60 | 0 | 90 | 0 |

| | | Tobacco budworm 3rd instar -ppm- | | | Cabbage looper 3rd instar -ppm- | | | German cockroach adult male | | | |
|---|---|---|---|---|---|---|---|---|---|---|---|
| R | 1000 | 100 | 10 | 1000 | 100 | 10 | Bait -ppm- 1000 | 100 | Residual -ppm- 1000 | 100 | | |
| $CF_3$ | 100 | 100 | 100<br>90<br>90 | 100 | 100 | 100<br>90<br>0 | 100 | 0 | 0 | | | |
| $CF_3O$ | 100 | 90 | 0 | 100 | 100 | 90 | 100 | 100 | 0 | | | |
| Br | 100 | 100 | 0 | 100 | 100 | 40 | 100 | 20 | 0 | | | |
| $CHF_2O$ | 100 | 100 | 0 | 100 | 30R** | 0 | 100 | 40 | 0 | | | |
| Cl | 100 | 100 | 0 | 100 | 100 | 70 | | | | | | |

*7 day residual test
**R = repellent
[(1)]A range is shown when more than ten insects are used in the test, and the mortality rate is less than 100%

EXAMPLE 8

By the methods described in detail in Example 7, the spiro cyclopropyl compounds of the present invention are compared to the corresponding spiro-cyclobutyl and -cyclopentyl analogs together with the corresponding unsubstituted and gem. dimethyl substituted compounds. The data obtained are summarized in Table III below, wherein it can be clearly seen that the spiro cyclopropyl compounds of the present invention are more effective for the control of lepidopterous insects, especially at lower rates of application, as are the above referred-to analogous compounds.

TABLE III (a)

Comparison of the efficacy of the spiro cyclopropyl compounds of the present invention to analogous compounds
Percent[1] mortality counts are given at the parts per million (ppm) concentrations shown

| Compound | Mosquito larvae -ppm- | | | Tobacco budworm 1st instar -ppm- | | Boll weevil adult -ppm- | | Southern armyworm 3rd instar -ppm- | | Tobacco budworm 3rd instar -ppm- | | Cabbage looper 3rd instar -ppm- | |
|---|---|---|---|---|---|---|---|---|---|---|---|---|---|
| | 1.2 | 0.4 | 0.04 | 300 | 10 | 1000 | 100 | 1000 | 10 | 1000 | 10 | 1000 | 10 |
| (CF₃)⟨phenyl⟩—CH=CH)₂C(=N—NH)—⟨gem-dimethyl⟩—N—H | 0 | 0 | | 100 | 0 | 0 | 0 | 100 | 40 | 100 | 0 | 100 | 0 |
| (CF₃)⟨phenyl⟩—CH=CH)₂C(=N—NH)—⟨cyclopropyl spiro⟩—N—H | 0 | | | 100 | 0 | 0 | 0 | 100 | 100 | 100 | 100 | 100 | 100 |
| (CF₃)⟨phenyl⟩—CH=CH)₂C(=N—NH)—⟨cyclobutyl spiro⟩—N—H | 0 | | | 100 | 35-45 | 0 | 40 | 100 | 100 | 100 | 100 | 100 | 100 |
| (CF₃)⟨phenyl⟩—CH=CH)₂C(=N—NH)—⟨cyclopentyl spiro⟩—N—H | 100 | 55-65 | | 85-95 R | 0 | 0 | 70 | 50 | 0 | 90 | 0 | 100 | 0 |
| (CF₃)⟨phenyl⟩—CH=CH)₂C(=N—NH)—⟨cyclohexyl⟩—N—H | 0 | | | 100 | 0 | 0 | 0 | 100 | 70 | 100 | 0 | 100 | 0 |

[1] A range is shown when more than ten insects are used in the test, and the mortality is less than 100%.
R = Repellent

TABLE III (b)

Comparison of the efficacy of the spiro cyclopropyl compounds of the present invention to analogous compounds
Percent[1] mortality counts are given at the parts per million (ppm) concentrations shown

| Compound | Mosquito larvae -ppm- | | | Tobacco budworm 1st instar -ppm- | | | Boll weevil adult -ppm- | |
|---|---|---|---|---|---|---|---|---|
| | 1.2 | 0.4 | 0.04 | 300 | 100 | 10 | 1000 | 100 |
| (Br—⟨C6H4⟩—CH=CH)₂C=N—NH—⟨ N=C(N-H)—C(CH₃)₂ (dimethyl cyclopropyl spiro) ⟩ | 0 | | | 100 | 100 | 0 | | 0 |
| (Br—⟨C6H4⟩—CH=CH)₂C=N—NH—⟨ N=C(N-H)—cyclopropyl spiro ⟩ | 0 | | | 100 | 100 | 65-75 | | 0 |
| (Br—⟨C6H4⟩—CH=CH)₂C=N—NH—⟨ N=C(N-H)—cyclobutyl ⟩ | 0 / 85-95 | | | 0 | | | 0 | |

| Compound | Southern armyworm 3rd instar -ppm- | | | Tobacco budworm 3rd instar -ppm- | | | Cabbage looper 3rd instar -ppm- | | |
|---|---|---|---|---|---|---|---|---|---|
| | 1000 | 100 | 10 | 1000 | 100 | 10 | 1000 | 100 | 10 |
| (Br—⟨C6H4⟩—CH=CH)₂C=N—NH—⟨ dimethyl cyclopropyl spiro ⟩ | 100 | 100 | 80 | 100 | 80 / 60 | 0 | 100 | 100 | 0 |
| (Br—⟨C6H4⟩—CH=CH)₂C=N—NH—⟨ cyclopropyl spiro ⟩ | 100 | 100 | 100 | 100 | 100 | 0 | 100 | 100 | 40 |
| (Br—⟨C6H4⟩—CH=CH)₂C=N—NH—⟨ cyclobutyl ⟩ | 100 | 100 | 0 | 10 R | 0 R | | 50 | 0 R | |

[1]A range is shown when more than ten insects are used in the test, and the mortality is less than 100%.
R = Repellent

TABLE III (c)

Comparsion of the efficacy of the spiro cyclopropyl compounds of the present invention to analogous compounds
Percent[1] mortality counts are given at the parts per million (ppm) concentrations shown

| Compound | Mosquito larvae -ppm- | | | Tobacco budworm 1st instar -ppm- | | | Boll weevil adult -ppm- | |
|---|---|---|---|---|---|---|---|---|
| | 1.2 | 0.4 | 0.04 | 300 | 100 | 10 | 1000 | 100 |

TABLE III (c)-continued

Comparsion of the efficacy of the spiro cyclopropyl compounds
of the present invention to analogous compounds
Percent[1] mortality counts are given at the parts per million (ppm) concentrations shown

| Compound | | | | | | | | | |
|---|---|---|---|---|---|---|---|---|---|
| (Cl—C₆H₄)—CH=CH)₂C=N—NH—[spiro gem-dimethyl cyclopropyl triazine] | 100 | 0 | | 100 | 55–65 | 0 | 0 | | 70 |
| (Cl—C₆H₄)—CH=CH)₂C=N—NH—[spiro cyclopropyl triazine] | 0 | | | 100 | 85–95 | 0 | 90 | | |
| (Cl—C₆H₄)—CH=CH)₂C=N—NH—[6-membered ring analog] | 35–45 | | | 0 | | | 0 | | |

| | Southern armyworm 3rd instar -ppm- | | | Tobacco budworm 3rd instar -ppm- | | | Cabbage looper 3rd instar -ppm- | | |
|---|---|---|---|---|---|---|---|---|---|
| Compound | 1000 | 100 | 10 | 1000 | 100 | 10 | 1000 | 100 | 10 |
| (Cl—C₆H₄)—CH=CH)₂C=N—NH—[spiro gem-dimethyl cyclopropyl triazine] | 100<br>100 | 100<br>100 | 100<br>0 | 100 | 40<br>100<br>50 | 0 | 100 | 100 | 0 |
| (Cl—C₆H₄)—CH=CH)₂C=N—NH—[spiro cyclopropyl triazine] | 100 | 100 | 50 | 100 | 100 | 0 | 100 | 100 | 60 |
| (Cl—C₆H₄)—CH=CH)₂C=N—NH—[6-membered ring analog] | 100 | 100 | 0 | 10<br>R | 90<br>0<br>R | | 100 | 60<br>40<br>R | |

[1]A range is shown when more than ten insects are used in the test, and the mortality is less than 100%.
R = Repellent

TABLE III (d)

Comparison of the efficacy of the spiro cyclopropyl compounds
of the present invention to analogous compounds
Percent[1] mortality counts are given at the parts per million (ppm) concentrations shown

| | Mosquito larvae -ppm- | | | Tobacco budworm 1st instar -ppm- | | | Boll weevil adult -ppm- | |
|---|---|---|---|---|---|---|---|---|
| Compound | 1.2 | 0.4 | 0.04 | 300 | 100 | 10 | 1000 | 100 |
| (CF₃O—C₆H₄)—CH=CH)₂C=N—NH—[spiro gem-dimethyl cyclopropyl triazine] | 0 | | | 100 | 0 | | 0 | |

TABLE III (d)-continued

Comparison of the efficacy of the spiro cyclopropyl compounds
of the present invention to analogous compounds
Percent[1] mortality counts are given at the parts per million (ppm) concentrations shown

| Compound | Southern armyworm 3rd instar -ppm- | | | Tobacco budworm 3rd instar -ppm- | | | Cabbage looper 3rd instar -ppm- | | |
|---|---|---|---|---|---|---|---|---|---|
|  | 1000 | 100 | 10 | 1000 | 100 | 10 | 1000 | 100 | 10 |
| (CF₃O—⟨⟩—CH=CH)₂C=N—NH—spiro | 0 | 100 | 100 | 0 | 50 | | | | |
| (CF₃O—⟨⟩—CH=CH)₂C=N—NH—spiro | 100 | 100 | 0 | 100 | 100 | 0 | 100 | 100 | 20 |
| (CF₃O—⟨⟩—CH=CH)₂C=N—NH—spiro | 100 | 100 | 100 | 100 | 90 | 0 | 100 | 100 | 90 |

[1] A range is shown when more than ten insects are used in the test, and the mortality is less than 100%.
R = Repellent
Subscripts "a", "b", "c" and "d" are used to indicated analogous subsets of the appropriate spiro cyclopropyl compounds according to the definition of Example 8.

We claim:

1. A compound having the structure:

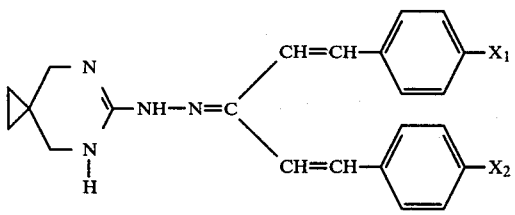

wherein $X_1$ and $X_2$ each are halogen, $CF_3$, $CHF_2O$, $CF_3O$, $CHF_2CF_2O$, $CHF_2S$, $C_1-C_3$ alkoxy or $C_2-C_3$ alkyl.

2. A compound according to claim 1, wherein $X_1$ and $X_2$ are each Br, Cl, $CF_3$, $CHF_2O$ or $CF_3O$.

3. A compound according to claim 1, wherein both $X_1$ and $X_2$ are the same and are Br, Cl, $CF_3$, $CHF_2O$ or $CF_3O$.

4. The compound according to claim 1, 1,5-bis(α,α,α-trifluoro-p-tolyl)-1,4-pentadien-3-one, 5,7-diazaspiro[2.5]oct-5-en-6-ylhydrazone.

5. The compound according to claim 1, 1,5-bis(p-chlorophenyl)1,4-pentadien-3-one,5,7-diazaspiro[2.5]oct-5-en-6-ylhydrazone.

6. The compound according to claim 1, 1,5-bis[p-(trifluoromethoxy)phenyl]-1,4-pentadien-3-one,5,7-diazaspiro[2.5]oct-5-en-6-ylhydrazone.

7. The compound according to claim 1, 1,5-bis(p-bromophenyl)1,4-pentadien-3-one,5,7-diazaspiro[2.5]oct-5-en-6-ylhydrazone.

8. The compound according to claim 1, 1,5-bis[p-(difluoromethoxy)phenyl]-1,4-pentadien-3-one,5,7-diazaspiro[2.5]oct-5-en-6-ylhydrazone.

9. A method for controlling insects comprising: contacting the insects, their habitat, and/or their food supply, with an insecticidally effective amount of a compound having the structure:

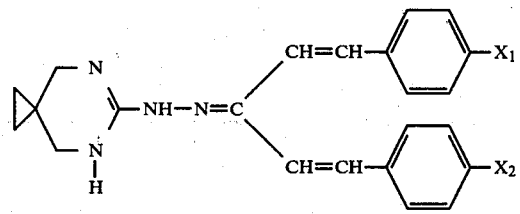

wherein $X_1$ and $X_2$ each are halogen, $CF_3$, $CHF_2O$, $CF_3O$, $CHF_2CF_2O$, $CHF_2S$, $C_1-C_3$ alkoxy or $C_2-C_4$ alkyl.

10. The method according to claim 9, wherein $X_1$ and $X_2$ each are Br, Cl, $CF_3$, $CHF_2O$ or $CF_3$.

11. The method according to claim 9, wherein both $X_1$ and $X_2$ are the same and are Br, Cl, $CF_3$, $CHF_2O$ or $CF_3O$.

12. The method according to claim 9, wherein the compound is 1,5-bis(α,α,α-trifluoro-p-tolyl)-1,4-pentadien-3-one,5,7-diazaspiro[2.5]oct-5-en-6-ylhydrazone.

13. The method according to claim 9, wherein the compound is 1,5-bis[p-(trifluoromethoxy)phenyl]-1,4-pentadien-3-one,5,7-diazaspiro [2.5]oct-5-en-6-ylhydrazone.

14. The method according to claim 9, wherein the compound is 1,5-bis(p-bromophenyl)-1,4-pentadien-3-one,5,7-diazaspiro[2.5]oct-5-en-6-ylhydrazone.

15. The method according to claim 9, wherein the compound is 1,5-bis[p-(difluoromethoxy)phenyl]-1,4-pentadien-3-one,5,7-diazaspiro [2.5]oct-5-en-6-ylhydrazone.

16. The method according to claim 9, wherein the insects are Lepidopterous insects, and the compound is applied at the rate of from 0.14 kg/hectare to 11.2 kg/hectare.

17. The method according to claim 9, wherein the insects are ants, Family Formicidae, and the compound is applied at the rate of from 2.5 g/hectare to 37.5 g/hectare.

18. The method according to claim 9, wherein the insects are termites, cockroaches, grasshoppers and ants, Family Formicidae, and the compound is applied incorporated in a bait at a concentration of from 0.125% to 2.0% by weight.

19. The method according to claim 17, wherein the ants are the southern fire ant *Solenopsis xyloni*, the black imported fire ant *Solenopsis richteri* and the red imported fire ant *Solenopsis invicta*.

20. A method for protecting agronomic crops, trees, shrubs and ornamentals from attack by insects comprising applying to said crops an insecticidally effective amount of a compound represented by formula:

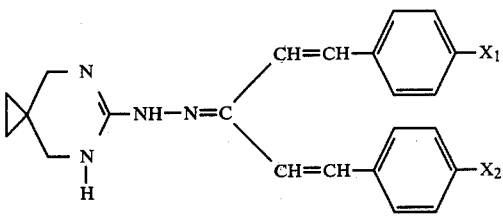

wherein $X_1$ and $X_2$ are each halogen, $CF_3$, $CHF_2O$, $CF_3O$, $CHF_2CH_2O$, $CHF_2S$, $C_1$-$C_3$ alkoxy or $C_2$-$C_4$ alkyl.

21. The method according to claim 20, wherein the insects are Lepidopterous insects, and the compound is applied at the rate of from 0.14 kg/hectare to 11.2 kg/hectare.

22. The method according to claim 20, wherein the insects are ants, Family Formicidae, and the compound is applied at the rate of from 2.5 g/hectare to 37.5 g/hectare.

23. The method according to claim 22, wherein the ants are the southern fire ant *Solenopsis xyloni*, the black imported fire ant *Solenopsis richteri* and the red imported fire ant *Solenopsis invicta*.

* * * * *

UNITED STATES PATENT AND TRADEMARK OFFICE
CERTIFICATE OF CORRECTION

PATENT NO. : 4,349,553
DATED : Sept. 14, 1982
INVENTOR(S) : Dale G. Brown

It is certified that error appears in the above—identified patent and that said Letters Patent is hereby corrected as shown below:

Column 1, lines 47-51, the structure should read as shown below.

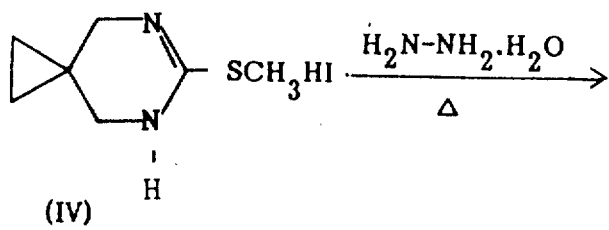

(IV)

Signed and Sealed this

Twenty-fifth Day of January 1983

[SEAL]

Attest:

GERALD J. MOSSINGHOFF

Attesting Officer    Commissioner of Patents and Trademarks